(12) United States Patent
Andersen et al.

(10) Patent No.: US 12,702,580 B2
(45) Date of Patent: Aug. 11, 2026

(54) OSTOMY APPLIANCE

(71) Applicant: Coloplast A/S, Humlebaek (DK)

(72) Inventors: Mikael Andersen, Alleroed (DK); Jeppe Marckmann, Kastrup (DK)

(73) Assignee: Coloplast A/S, Humlebaek (DK)

( * ) Notice: Subject to any disclaimer, the term of this patent is extended or adjusted under 35 U.S.C. 154(b) by 525 days.

(21) Appl. No.: 18/036,171

(22) PCT Filed: Nov. 12, 2021

(86) PCT No.: PCT/DK2021/050331

§ 371 (c)(1),
(2) Date: May 10, 2023

(87) PCT Pub. No.: WO2022/100804

PCT Pub. Date: May 19, 2022

(65) Prior Publication Data

US 2023/0404789 A1 Dec. 21, 2023

(30) Foreign Application Priority Data

Nov. 12, 2020 (DK) ........................... PA 2020 70751

(51) Int. Cl.
*A61F 5/445* (2006.01)
*A61F 5/44* (2006.01)
*A61F 5/448* (2006.01)

(52) U.S. Cl.
CPC ............ *A61F 5/445* (2013.01); *A61F 5/4404* (2013.01); *A61F 2005/4486* (2013.01)

(58) Field of Classification Search
CPC . A61F 5/445; A61F 5/4404; A61F 2005/4486
See application file for complete search history.

(56) References Cited

U.S. PATENT DOCUMENTS 2,796,063 A * 6/1957 Smelser .................. A61F 5/448 604/342
3,042,430 A * 7/1962 Guy ........................ F16L 23/06 24/270

(Continued)

FOREIGN PATENT DOCUMENTS

EP 0373782 A1 6/1990
FR 2690333 A1 10/1993
GB 2296662 A 7/1996

*Primary Examiner* — Guy K Townsend
(74) *Attorney, Agent, or Firm* — Coloplast Corp., Coloplast A/S; Nick Baumann

(57) ABSTRACT

An ostomy appliance (10) comprising a base plate (20) with a first coupling part (40), a collecting bag (30) with a second coupling part (50), the first coupling part (40) and the second coupling part (50) being configured for cooperating with each other so as to provide a coupling between the collecting bag and the base plate; the first coupling part (40) comprises a first coupling ring (41) comprising an axially extending first flange (42), the axially extending first flange (42) comprises an outer contact face (44) and a ring collar (45), the ring collar is positioned on the distal part of axially extending first flange (42), the distal surface of the ring collar (45) having a first diameter; the second coupling part (50) comprises a second coupling ring (51) comprising an axially extending lock flange (53), the axially extending lock flange (53) of the second coupling part (50) comprises an inner lock contact face (54) having a second diameter; the second coupling part (50) comprises a radially extending second flange (52) and a sealing ring (55) adapted for sealing between the first coupling part (40) and the second coupling part (50), wherein the sealing ring (55) is adapted for being positioned at a distal surface on the ring collar (45) of the axially extending first flange (42) so as to provide a seal.

16 Claims, 6 Drawing Sheets

(56) References Cited

U.S. PATENT DOCUMENTS 3,276,089 A * 10/1966 Cheever .................. F16L 33/12 24/270
4,710,183 A 12/1987 Steer
4,828,553 A * 5/1989 Nielsen ................... A61F 5/448 604/339
4,963,136 A * 10/1990 Steer ....................... A61F 5/448 604/339
5,322,523 A * 6/1994 Olsen ...................... A61F 5/448 604/338
5,496,297 A * 3/1996 Olsen ...................... A61F 5/448 604/338
5,520,670 A 5/1996 Blum
5,549,588 A 8/1996 Johnsen
5,647,861 A 7/1997 Steer et al.
5,843,053 A * 12/1998 Steer ....................... A61F 5/448 604/338
5,902,295 A * 5/1999 Steer ....................... A61F 5/448 604/338
10,010,443 B2 * 7/2018 Becker .................... A61F 5/448
10,034,792 B2 * 7/2018 Pedersen ................. A61F 5/448
2009/0118687 A1 * 5/2009 Kristensen .............. A61F 5/448 604/342
2009/0163886 A1 * 6/2009 Therkelsen ............. A61F 5/448 604/342
2014/0148771 A1 5/2014 Luce
2014/0324003 A1 * 10/2014 Becker .................... A61F 5/448 604/342
2015/0045755 A1 * 2/2015 Pedersen ................. A61F 5/448 604/342
2015/0359658 A1 * 12/2015 Leise, Jr. ................ A61F 5/448 604/342
2018/0296384 A1 10/2018 O'Brien
2021/0259875 A1 * 8/2021 Holroyd .................. A61F 5/448
2023/0404789 A1 * 12/2023 Andersen .............. A61F 5/4404

* cited by examiner

OSTOMY APPLIANCE

The invention relates to an ostomy appliance.

BRIEF DESCRIPTION OF THE DRAWING

The accompanying drawings are included to provide a further understanding of embodiments and are incorporated into and a part of this specification. The drawings illustrate embodiments and together with the description explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
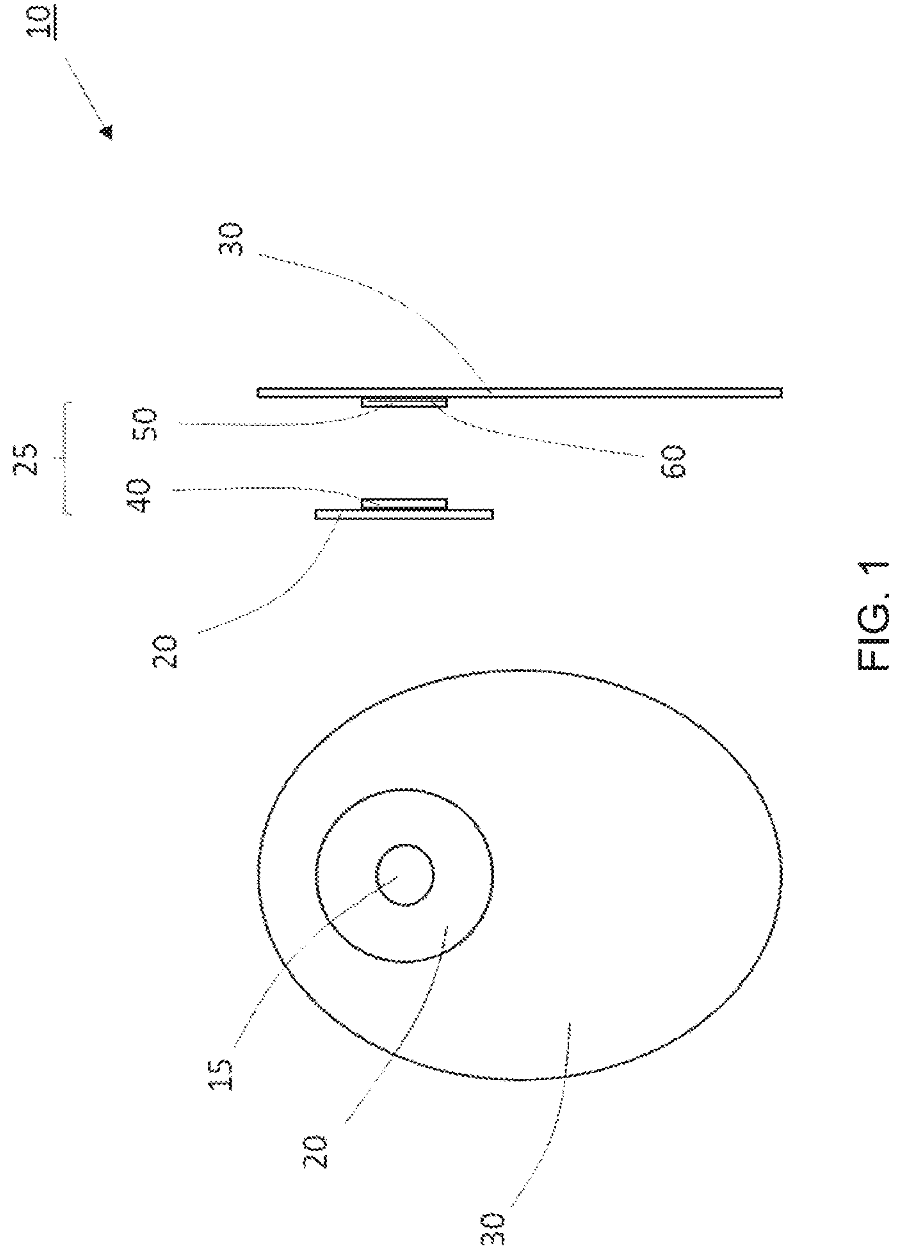
FIG. 1 illustrates two schematic side views of an ostomy appliance.

Embodiments, and features of the various exemplary embodiments described in this application, may be combined with each other ("mixed and matched"), unless specifically noted otherwise.

In the following detailed description, reference is made to the accompanying drawings, which form a part hereof, and in which is shown by way of illustration specific embodiments in which the invention may be practiced. Because components of embodiments can be positioned in different orientations, the directional terminology is used for purposes of illustration and is in no way limiting. It is to be understood that other embodiments may be utilized, and structural or logical changes may be made without departing from the scope of the present invention. Therefore, the following detailed description is not to be taken in a limiting sense, and the scope of the present invention is defined by the appended claims.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma when the appliance is worn by a user. Thus, the axial direction is substantially perpendicular to the abdominal surface of the user.

The radial direction is defined as transverse to the axial direction that is transversely to the direction of the stoma. Thus, the radial direction is substantially perpendicular to the stoma of the user.

The words "inner" and "outer" may be used. These qualifiers should generally be perceived with respect to the radial or axial direction, such that a reference to an "outer" element means that the element is farther away from a centre portion of the ostomy appliance than an element referenced as "inner."

The term diameter of a disclosed element is defined as the length of a line between two points of the element in radially direction though a centre portion of the ostomy appliance. Thus, the diameter is a line substantially parallel with the abdominal surface of the user when the appliance is worn by the user. Thus, the radius of a diameter is measured from the centre of a stoma/the midpoint of a central opening of the coupling parts and radially outwards.

A two-part coupling for ostomy appliances may be provided in a selection of ranges corresponding to sizes of base plates and collection bags collections. The range may provide coupling parts having a central opening having a diameter of approximately 40-70 mm corresponding to a selection of different sizes of ostomy appliances.

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time. The solid and liquid wastes emanating from the stoma may be referred to as stoma output.

The ostomy appliance may be a two-piece appliance comprising a base plate and a collecting bag which may be coupled to and un-coupled from each other through a coupling means. This has the effect that the base plate does not need to be separated from the skin of the user as often as exchange of the collecting bag requires. The base plate may need only to be changed every third or fourth day depending on the user, whereas the collecting bag may be changed more than once per day. Typically, it is desirable to need as few exchanges of the base plate as possible in order to reduce the risk of skin complications.

A two-part coupling adapted to releasable attach a collecting bag to a base plate may be difficult to handle. It may require a special technique to connect the collecting bag to a base plate or even a significant amount of pressure may be required to press the coupling parts together and thereby attach the collecting bag to the base plate.

The abdomen and the peristomal skin are often relatively soft and flexible, and tests have shown that it may be difficult to allow engagement of two coupling parts by applying a force towards the abdomen in axial direction, as the abdomen may not be able to comfortably provide a counter pressure allowing the coupling parts to engage properly. Additionally, since the skin surrounding a stoma may be sensitive, particularly in the time period following the surgical procedure creating the stoma, applying a force to the skin resulting in the skin and abdomen to be significantly depressed may be painful and may even be destructive to the skin.

The amount of force necessary to engage and/or disengage the coupling parts is determined by the structure of the coupling parts and is a function of the amount of force necessary to frictionally engage the coupling parts of the collecting bag and the base plate, which in turn, is limited, as indicated above, by the amount of force which can be acceptably applied to the skin (of the user) under the base plate.

When coupling a two-part coupling it can be difficult to locate the two coupling parts in relation to each other by matching the two coupling parts, and it is preferable that the user may get a feedback, such as a click-feedback by sense and/or sound, to be sure that the two coupling parts are coupled together correctly.

Therefore, there is a need for providing a releasable coupling that is intuitive to couple and easy to use and that require minimal work and still feels secure in respect of avoidance of unintended release of the coupling and hence the risk of subsequent leakage.

This is obtained by an ostomy appliance comprising a base plate with a first coupling part, a collecting bag with a second coupling part, the first coupling part and the second coupling part being configured for cooperating with each other so as to provide a coupling between the collecting bag and the base plate; the first coupling part comprises a first coupling ring comprising an axially extending first flange, the axially extending first flange comprises an outer contact face and a ring collar, the ring collar is positioned on a distal part of the axially extending first flange, the distal surface of the ring collar having a first diameter; the second coupling part comprises a second coupling ring comprising an axially extending lock flange, the axially extending lock flange of the second coupling part comprises an inner lock contact face having a second diameter; the second coupling part comprises a radially extending second flange and a sealing ring adapted for sealing between the first coupling part and the second coupling part, wherein the sealing ring is adapted for being positioned at the distal surface on the ring collar of the axially extending first flange so as to provide a seal.

Hereby is achieved a coupling that is intuitive and easy to use.

As the area for sealing is relocated, the sealing ring need not to be pressed past the outer face of the first coupling part. In addition, the sealing forces extend mainly in axial direction and not in radial direction as the locking forces. Thus, the distribution of forces relating to coupling, locking and sealing are offset and angled in different directions.

In embodiments, the radially extending second flange extends radially inwards and the sealing ring is positioned on the inner part of the radially extending second flange.

In embodiments, the second diameter is the same or smaller than the first diameter.

Generally, the first diameter and the second diameter may be in the range of approximately 40-70 mm. The second diameter may be the same as the first diameter or up to 10 mm smaller than the first diameter. In an embodiment, the first diameter may be 52 mm and the second diameter may be 50 mm. In another embodiment, the first diameter may be 42 mm and the second diameter may be 40 mm.

In embodiments, the second diameter is 0, 1-9 mm smaller, such as 0, 2-8 mm smaller, such as 0, 3-7 mm smaller, such as 0, 4-6 mm smaller, such as 0, 5-5 mm smaller, such as mm smaller, such as 0, 7-3 mm smaller than the first diameter.

In embodiments, the first coupling part is a male coupling, and the second coupling part is a female coupling.

In embodiments, the outer contact face of the axially extending first flange and the inner lock contact face of the axially extending lock flange are abutting, when the first coupling part and the second coupling part are connected.

In embodiments, the second coupling part comprises a locking ring. Hereby the locking ring may clamp the first and second coupling part into locking position after the two coupling parts are mutually coupled.

The sealing ring extends continuously around the coupling part on the distal part of the axially extending first flange. In embodiments, the diameter of the sealing ring is smaller than the diameter of the inner contact face of the second coupling part.

In embodiments, the sealing ring is made of plastic material, thermoplastic elastomer, polyurethane, such as TPE or Poron. Especially rubberlike materials are able to be squeezed together to form a seal that is liquid tight.

In embodiments, the second coupling ring and the sealing ring are made of the same material.

In embodiments, the first coupling part comprises a soft sealing part and a more rigid stabilising part formed by the radially extending first flange and the ring collar, the ring collar forms the soft sealing part, which is positioned radially outwards on the stabilising part formed by the radially extending first flange. The ring collar may be an integral part of the stabilising part.

In embodiments, the ring collar extends radially outwards to form an indentation for providing a snap-fit connection.

In embodiments, the second coupling part comprises two locking flanges, a radially extending proximal locking flange and a radially extending distal locking flange, the two locking flanges extending radially outwards from the radially extending second flange defining a locking groove.

In embodiments, the radially extending proximal locking flange comprises two or more slits in radial direction. Hereby is achieved a more flexible coupling ring, which is therefore easier to press into locking position.

In embodiments, the two or more slits are extended axially into the radially extending second flange.

In embodiments, the two or more slits are evenly distributed along the periphery of the radially extending proximal locking flange. Hereby, a more flexible flange is obtained, and the coupling requires less forces when the two coupling parts are being connected.

In embodiments, the second coupling part comprises 6 slits evenly distributed along the periphery. The slits may comprise a width along the periphery of 2-6 mm, such as 3-5 mm, such as 4 mm. In embodiments, the appliance comprises 4, 6 or 8 slits evenly distributed along the periphery.

Generally, an ostomy appliance comprising a base plate with a first coupling part, a collecting bag with a second coupling part, the first coupling part and the second coupling part being configured for cooperating with each other so as to provide a coupling between the collecting bag and the base plate; the first coupling part comprises a first coupling ring comprising an axially extending first flange, the axially extending first flange comprises an outer contact face and a ring collar, the ring collar is positioned on a distal part of the axially extending first flange; the second coupling part comprises a second coupling ring comprising an axially extending lock flange; the second coupling part comprises a radially extending second flange and a sealing ring adapted for sealing between the first coupling part and the second coupling part, wherein the sealing ring is adapted for being positioned at the distal surface on the ring collar of the axially extending first flange so as to provide a seal.

DETAILED DESCRIPTION OF THE DRAWING

FIG. 1 illustrates two schematic side views of an ostomy appliance 10 comprising a base plate 20 with a first coupling part 40 and a collecting bag 30 with a second coupling part 50. The first coupling part 40 and the second coupling part

50 are adapted for cooperating with each other to provide a two-part coupling 25 between the collecting bag and the base plate.

The base plate 20 comprises a through-going stoma opening 15. The stoma opening is configured to receive a stoma of the user and/or the stoma opening is configured to allow output from the stoma to pass through the stoma opening 15 and into a collecting bag 30 attached to the base plate 20. The stoma opening is configured to allow passage of output from a proximal side of the base plate 20 to a distal side of the base plate and inside the collecting bag 30.

Figure 2:
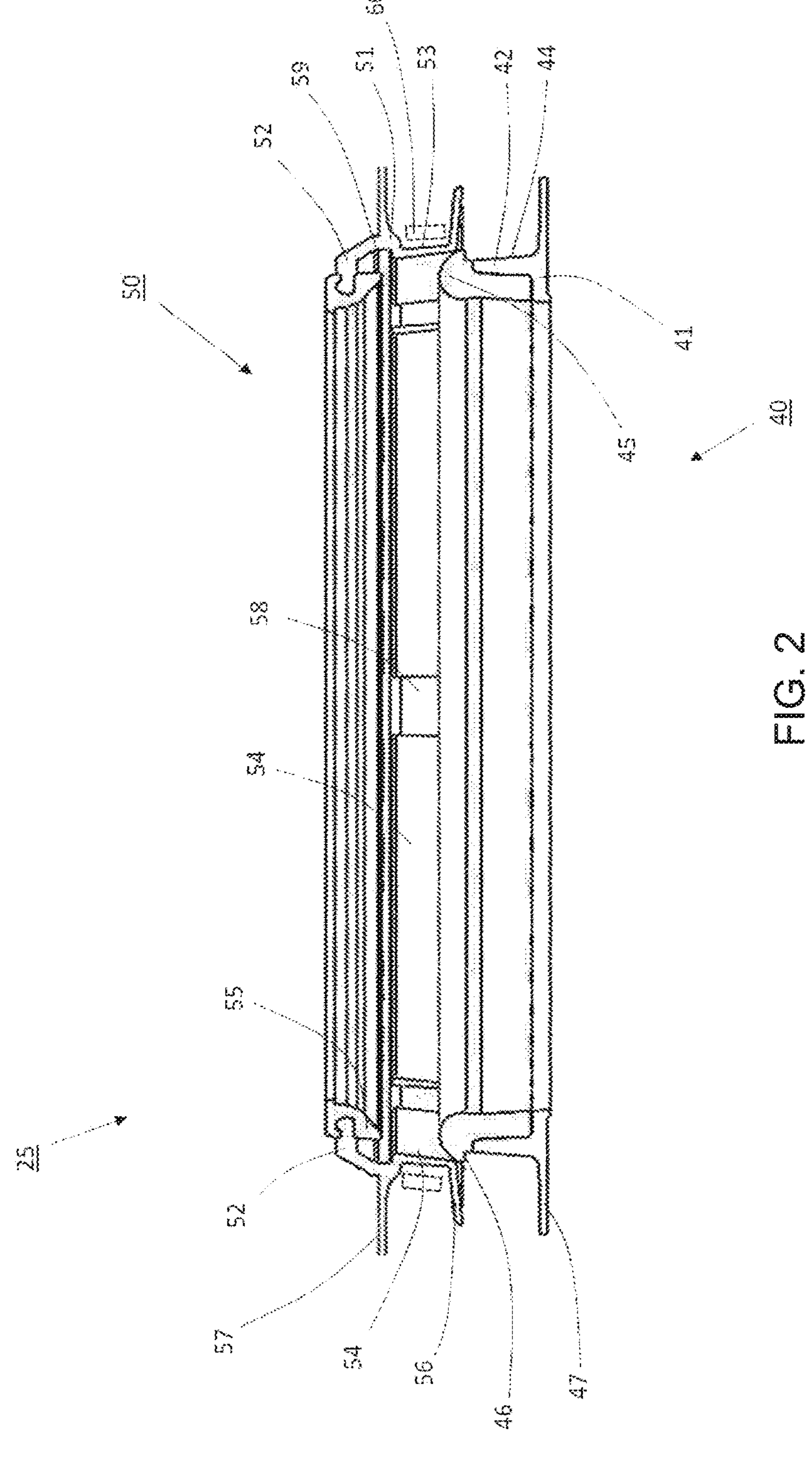
FIG. 2 illustrates a cross-sectional side view of a two-part coupling for an ostomy appliance.

FIG. 2 illustrates a cross-sectional side view of a two-part coupling 25 for an ostomy appliance prior to locking position. The two-part coupling comprises two annular coupling parts, a first coupling part 40 and a second coupling part 50.

The first coupling part 40 comprises a first coupling ring 41 with an axially extending first flange 42 forming a male coupling. The axially extending first flange comprises an outer locking contact face 44 and a ring collar 45. The ring collar 45 is positioned on a distal part of the axially extending first flange 42. The ring collar 45 comprises a ring-shape and a sealing ring of the second coupling part 50 is adapted for being positioned at the distal surface of the ring collar 45. wherein the sealing ring 55 is adapted for being positioned at a distal surface on the ring collar 45 of the axially extending first flange 42 so as to provide a seal.

The most distal part of the curved ring collar 45 has a first diameter. The outer locking contact face 44 has a larger diameter than the first diameter.

The second coupling part 50 comprises a second coupling ring 51 and an axially extending lock flange 53, the axially extending lock flange 53 of the second coupling part comprises an inner lock contact face 54 having a second diameter. The second coupling part 50 forming a female coupling being complementary shaped to the first coupling part 40.

The second coupling part 50 comprises a radially inwardly extending second flange 52 and a sealing ring 55 positioned on a distal part of the second flange 52. The sealing ring is adapted for being positioned on the ring collar 45 of the first flange 42 for sealing between the first coupling part 40 and second coupling parts 50.

The first coupling ring 41 comprises a radially outwardly extending proximal flange 47. The ring collar 45 on the first coupling part 40 comprises an outwardly extending rim 46. When the male and female couplings are in locking position the surfaces of the proximal flange 47, the locking contact face 44 and the ring collar 45 provides a contact surface for being positioned against a second contact surface of the second coupling ring 51. The second contact surface of the second coupling ring 51 is formed by the surfaces formed by the axially extending lock flange 53, the radially extending proximal locking flange 56 and the radially extending distal locking flange 57.

The first coupling part 40 is shaped as a male coupling and the second coupling part 50 is shaped as a female coupling.

The female coupling (the second coupling part) is made of flexible material to allow snap fit connection with the male coupling. The flexibility of the female coupling is enhanced by a number of slits 58 evenly distributed around the second coupling ring 51.

The slits 58 are formed in the axially extending lock flange 53 and in the radially extending proximal locking flange 56 allowing the flanges 53,56 to flex outwardly and allow the second coupling ring 51 to pass over the outwardly extending collar rim 46 of the first coupling 40 part. As the axially extending lock flange 53 and in the radially extending proximal locking flange 56 flexes back outwardly, the female coupling slides over the male coupling and the inner face 54 of the second coupling part juxtaposes the outer locking contact face 44 of the first coupling part 40. Thereafter, a locking ring 60 may be tightened by decrease the diameter, by decreasing the circumference of the locking ring clamp the inner face 54 against the outer face 44 for locking the female coupling to the male coupling, and thereby couple the collecting bag to a base plate. The locking ring 60 is illustrated schematically only in dotted lines.

Furthermore, the second coupling part 50 comprises a groove 59 for accommodating the rim 46 of the ring collar 45.

The radially extending flanges and the rim 46 of the ring collar 45 may give a click response to the user, when the female coupling is snapped into position, and thereby allowing the user to acknowledge a correct coupling has occurred. In locking position, the inner face 54 is clamped toward the outer face 44 by the locking ring 60, and the sealing ring 55 is positioned on an inner part of radially extending second flange 52 forming a seal between the male and female coupling. The sealing ring may be formed of a flexible plastic material, such as a soft TPE.

In the figures the second coupling part 50 is positioned juxtaposed the first coupling part prior to being pressed info locking position.

The diameter of the distal surface of the ring collar 45 is smaller than the diameter of the inner contact face 54 and outer face 44. The diameter of the sealing ring 55 is smaller than the diameter of the inner contact face 54 of the second coupling part 50.

Figure 3:
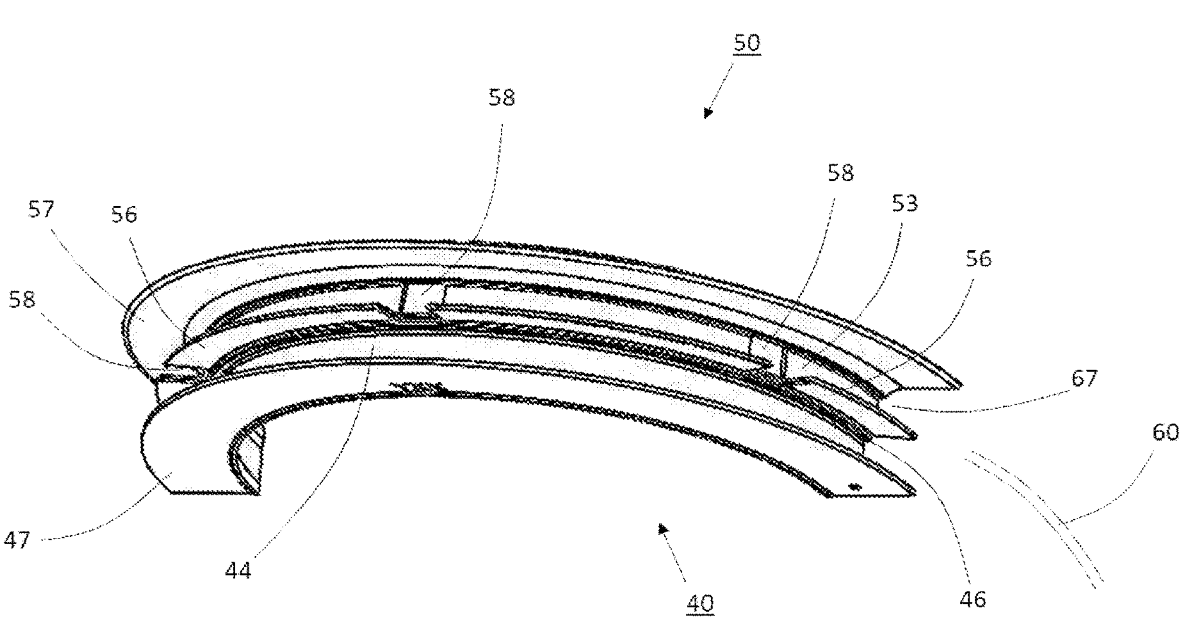
FIG. 3 illustrates part of a two-part coupling as illustrated in FIG. 2 seen in a perspective view.

FIG. 3 illustrates part of a two-part coupling as illustrated in FIG. 2 seen in a perspective view prior to locking position. In this view it is clearly that the slits 58 are formed in the axially extending first flange lock 53 and in the radially extending proximal locking flange 56 allowing both flanges 53,56 to flex outwardly and allow the second coupling ring 51 to pass over the male coupling. The axially extending lock flange 53 may function as a guide during coupling.

Figure 4:
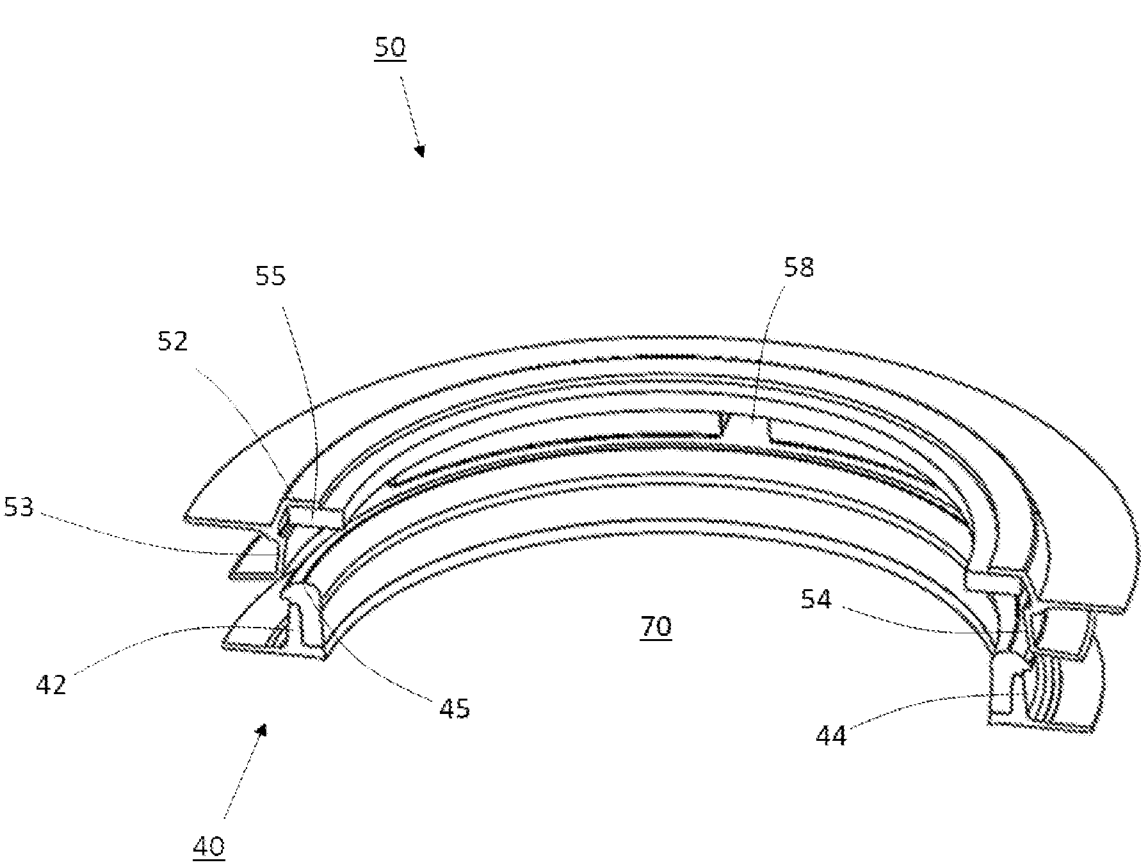
FIG. 4 illustrates part of a two-part coupling in a perspective view.

FIG. 4 illustrates part of a two-part coupling in a perspective view. The cross-sectional view illustrates that the sealing ring 55 is made of a gasket. The gasket is positioned on the inner face of the radially extending flange 52 and seals the connection of the first coupling part 40 and the second coupling part 50. The gasket may be an annular shaped foam.

The male and female coupling parts of the two-part coupling comprises inherently a central opening 70 to accommodate the through-going stoma opening 15 and allow a stoma of the user and/or output from the stoma to pass through the stoma opening 15 and the central opening 70 formed by the ring-shaped coupling parts and into an collecting bag 30 attached to the base plate 20.

Figure 5:
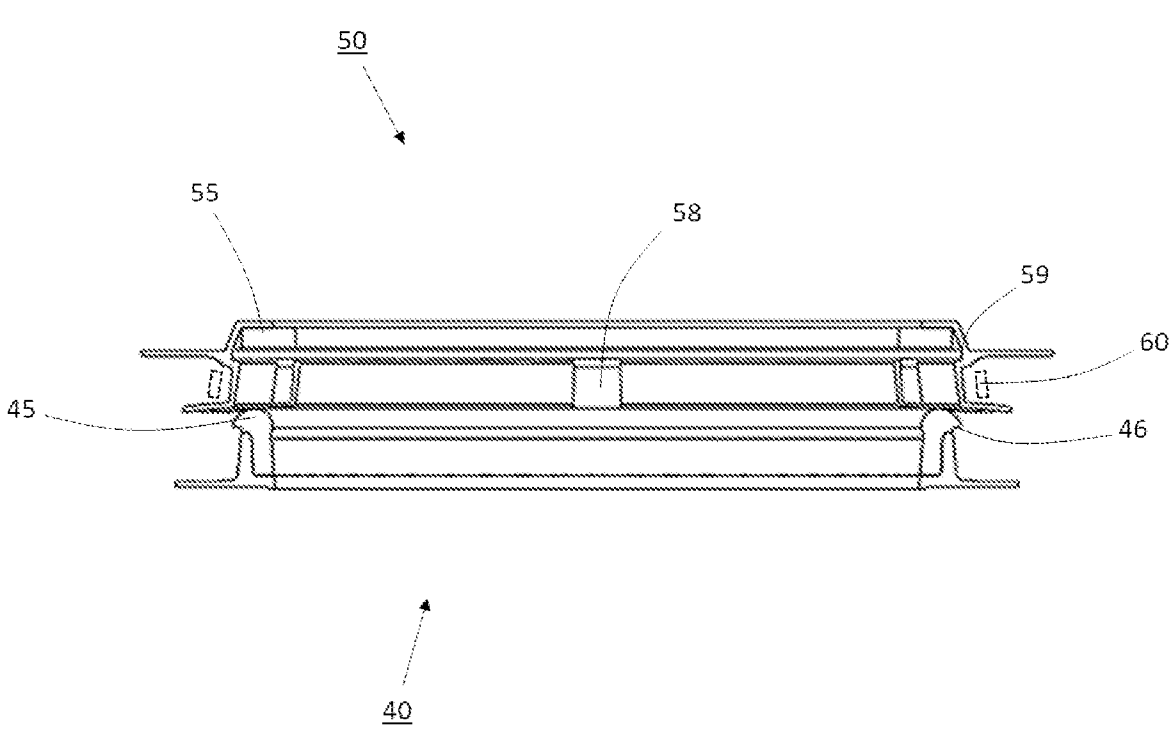
FIG. 5 illustrates a side view of the two-part coupling illustrated in FIG. 4.

FIG. 5 illustrates a side view of the two-part coupling illustrated in FIG. 4. The sealing ring illustrated in FIGS. 4 and 5 and the radially extending second flange 52 has been modified otherwise the two-part coupling comprises similar features as illustrated in the embodiment shown in FIGS. 2 and 3.

The second coupling part 50 comprises a second coupling ring 51 and an axially extending lock flange 53, the axially extending lock flange 53 of the second coupling part comprises an inner lock contact face 54 having a second diameter. The second coupling part 50 forms a female coupling being complementary shaped to the first coupling part 40.

The second coupling part 50 comprises a radially inwardly extending second flange 52 and a sealing ring 55 positioned on a distal part of the second flange 52. The sealing ring 55 is adapted for being positioned on the ring collar 45 of the first flange 42 for sealing between the first coupling part 40 and second coupling part 50.

The first coupling ring 41 comprises a radially outwardly extending proximal flange 47. The ring collar 45 on the first coupling part 40 comprises a radially outwardly extending rim 46. When the male and female couplings are in locking position the surfaces of the lock flange 47, the locking contact face 44 and the ring collar 45 provides a contact surface for being positioned against a second contact surface of the second coupling ring 51.

The second contact surface of the second coupling ring 51 is formed by the surfaces formed by the axially extending lock flange 53, the radially extending proximal locking flange 56 and the axially extending distal locking flange 57.

The female coupling is made of flexible material to allow snap fit connection with the male coupling. The flexibility of the female coupling is enhanced by a number of slits 58 evenly distributed around the second coupling ring 51.

The slits 58 are formed in the axially extending lock flange 53 and in the radially extending proximal locking flange 56 allowing the flanges 53,56 to flex outwardly and allow the second coupling ring 51 to move past the outwardly extending collar rim 46 of the first coupling 40 part. As the axially extending lock flange 53 and in the radially extending proximal locking flange 56 flexes back outwardly, the female coupling slides over the male coupling and the inner face 54 of the second coupling part juxtaposes the outer locking contact face 44 of the first coupling part 40. Thereafter, a locking ring 60 may be tightened by decreasing the diameter and by decreasing the circumference of the locking ring, clamp the inner face 54 against the outer face 44 for locking the female coupling to the male coupling, and thereby couple the collecting bag to a base plate. The locking ring 60 is illustrated schematically only in dotted lines.

Furthermore, the second coupling part 50 is provided with a groove 59 for accommodating the rim 46 of the ring collar 45.

Figure 6:
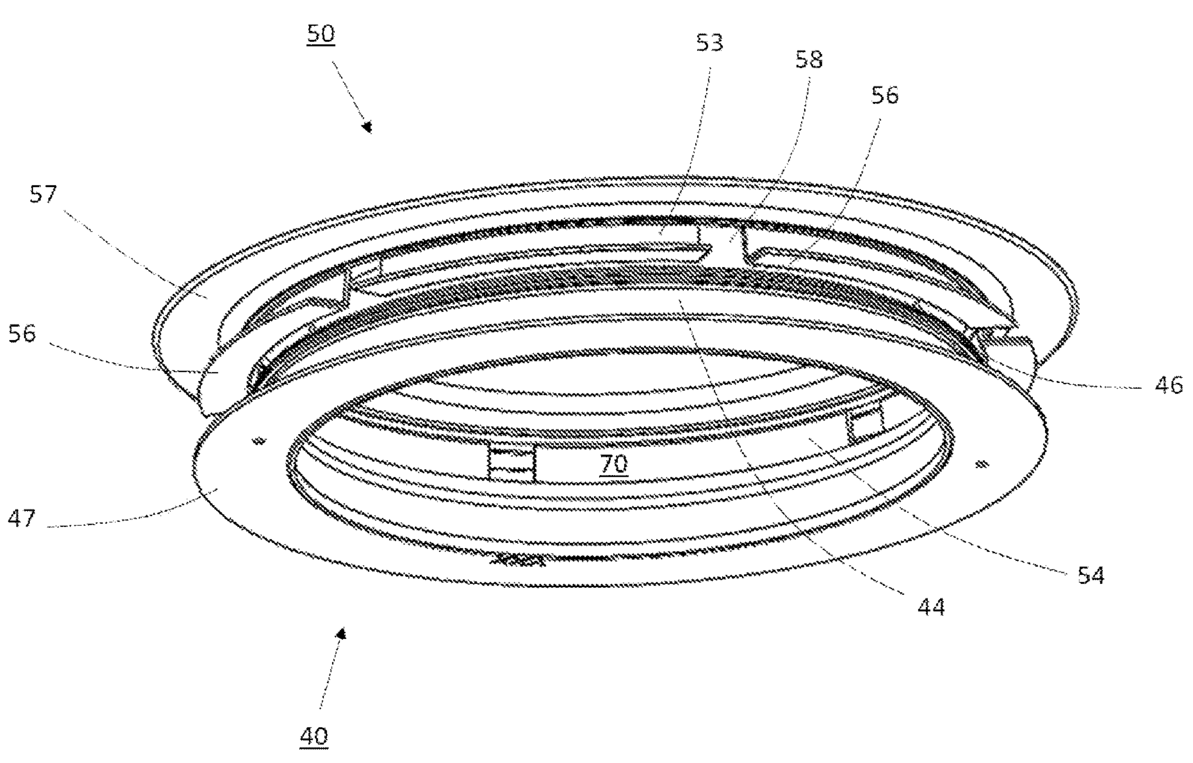
FIG. 6 illustrates a perspective view of the two-part coupling illustrated in FIGS. 4 and 5.

FIG. 6 illustrates a perspective view of the two-part coupling illustrated in FIGS. 4 and 5. The annular ring-shaped couplings (40,50) comprises a central opening 70.

FIG. 6 clearly illustrates the slits 58 formed in the radially extending proximal locking flange 56 and the axially extending lock flange 53, which allow the flanges to more easily flex outwardly, when the two coupling parts are pressed together.

Embodiments, and features of the various exemplary embodiments descry-bed in this application, may be combined with each other ("mixed and matched"), unless specifically noted otherwise.

The invention claimed is:

1. An ostomy appliance comprising:

a base plate comprising a first coupling part; and a collecting bag connected to a second coupling part;

the first coupling part comprises an integrated first coupling ring comprising:

a radially outwardly extending proximal flange, an axially extending first flange comprising an outer contact face, and a ring collar integrated on a distal part of the axially extending first flange, with a distal surface of the ring collar having a first diameter;

the second coupling part comprises an integrated second coupling ring comprising:

a radially outwardly extending distal locking flange, an axially extending lock flange comprising an inner lock contact face having a second diameter, and a radially inwardly extending second flange forming comprising a sealing ring that forms a groove distal to the inner lock contact face;

wherein the radially outwardly extending proximal flange of the integrated first coupling ring is a continuously endless first ring;

wherein the radially outwardly extending distal locking flange of the integrated second coupling ring is a continuously endless second ring.

2. The ostomy appliance according to claim 1, wherein the second diameter is equal to or smaller than the first diameter.

3. The ostomy appliance according to claim 1, wherein the base plate is attachable to skin of a user and the first coupling part is a male coupling projecting from the base plate, and the second coupling part is a female coupling adapted to receive the male coupling to allow the collecting bag to be attached to and removed from the base plate with the base plate attached to the skin.

4. The ostomy appliance according to claim 1, wherein, when the first coupling part and the second coupling part are connected, the outer contact face of the axially extending first flange and the inner lock contact face of the axially extending lock flange abut.

5. The ostomy appliance according to claim 1, wherein the continuously endless second ring is deformable and flexible to allow the ring collar of the integrated first coupling ring to be inserted into the groove of the sealing ring of the continuously endless second ring.

6. The ostomy appliance according to claim 1, wherein the sealing ring of the radially inwardly extending second flange extends inward relative to the second diameter of the inner lock contact face.

7. The ostomy appliance according to claim 1, wherein the sealing ring comprises one of a plastic material, a thermoplastic elastomer, and a polyurethane.

8. The ostomy appliance according to claim 1, wherein the radially outwardly extending distal locking flange and the radially inwardly extending second flange of the second coupling ring are made of the same material.

9. The ostomy appliance according to claim 1, wherein the first coupling ring comprises a soft sealing part and a stabilising part more rigid than the soft sealing part, the stabilising part formed by the axially extending first flange and the soft sealing part formed by the ring collar, with the ring collar positioned radially outwards on the stabilising part.

10. The ostomy appliance according to claim 1, wherein the ring collar extends radially outwards to form an indentation adapted to snap-fit with the groove of the sealing ring.

11. The ostomy appliance according to claim 1, wherein the second coupling part comprises two radially outwardly extending locking flanges including a radially outwardly extending proximal locking flange spaced a distance from the radially outwardly extending distal locking flange, the two radially outwardly extending locking flanges extending radially outwards relative to the groove and the inner look contact face.

12. The ostomy appliance according to claim 11, wherein the radially outwardly extending proximal locking flange comprises two or more slits in radial direction.

13. The ostomy appliance according to claim 12, wherein the two or more slits extended into the axially extending lock flange.

14. The ostomy appliance according to claim 12, wherein the two or more slits are evenly distributed along a periphery of the radially outwardly extending proximal locking flange.

15. The ostomy appliance of claim 1, wherein the integrated second coupling ring further comprises a radially outwardly extending proximal locking flange located proximal the inner lock contact face;

wherein slits are formed in each of the axially extending lock flange and the radially outwardly extending proximal locking flange to allow the integrated second coupling ring to flex when the second coupling part is secured to the first coupling part.

16. The ostomy appliance according to claim 1, wherein, when the first coupling part and the second coupling part are connected, the ring collar of the first coupling part engages with the groove of the sealing ring of the second coupling part.

* * * * *